United States Patent
Kador (10) Patent No.: US 9,173,915 B1
(45) Date of Patent: Nov. 3, 2015

(54) ANTIOXIDANT EYE DROPS

(71) Applicant: Peter F. Kador, Omaha, NE (US)

(72) Inventor: Peter F. Kador, Omaha, NE (US)

(*) Notice: Subject to any disclaimer, the term of this patent is extended or adjusted under 35 U.S.C. 154(b) by 0 days.

(21) Appl. No.: 14/512,365

(22) Filed: Oct. 10, 2014

(51) Int. Cl.
| | |
|---|---|
| A01N 65/00 | (2009.01) |
| A61K 36/82 | (2006.01) |
| A61K 31/122 | (2006.01) |
| A61K 31/05 | (2006.01) |
| A61K 31/19 | (2006.01) |
| A61K 31/353 | (2006.01) |
| A61K 47/32 | (2006.01) |
| A61K 47/26 | (2006.01) |
| A61K 47/18 | (2006.01) |
| A61K 9/00 | (2006.01) |
| A61K 36/00 | (2006.01) |

(52) U.S. Cl.
CPC .............. *A61K 36/82* (2013.01); *A61K 9/0048* (2013.01); *A61K 31/05* (2013.01); *A61K 31/122* (2013.01); *A61K 31/19* (2013.01); *A61K 31/353* (2013.01); *A61K 36/00* (2013.01); *A61K 47/183* (2013.01); *A61K 47/186* (2013.01); *A61K 47/26* (2013.01); *A61K 47/32* (2013.01)

(58) Field of Classification Search
CPC ...................................................... A61K 36/00
USPC ....................................................... 424/725
See application file for complete search history.

(56) References Cited

U.S. PATENT DOCUMENTS

| | | |
|---|---|---|
| 5,527,533 A | 6/1996 | Tso et al. |
| 5,817,630 A | 10/1998 | Hofmann et al. |
| 7,655,698 B2 | 2/2010 | Koverech et al. |
| 2006/0111318 A1 | 5/2006 | Okamoto |
| 2006/0217445 A1 | 9/2006 | Chew et al. |
| 2009/0068255 A1 | 3/2009 | Yu et al. |
| 2009/0253745 A1 | 10/2009 | Mata et al. |
| 2010/0093648 A1 | 4/2010 | Cruz |
| 2011/0034554 A1 | 2/2011 | Washington |
| 2011/0237548 A1 | 9/2011 | Minatelli et al. |

FOREIGN PATENT DOCUMENTS

JP          2009-196903          9/2009

*Primary Examiner* — Michael Meller
(74) *Attorney, Agent, or Firm* — Richard C. Litman (57) ABSTRACT

The antioxidant eye drops is a topical ophthalmic formulation that contains four nutraceuticals (namely, astaxanthin, resveratrol, pyruvate and epigallocatechin gallate (EGCG)) having antioxidant, anti-inflammatory, and chelating activity in a carbomer gel carrier. The active ingredients can reduce oxidative stress through free radical scavenging and chelating activity. The carrier is composed of a solution of deionized water containing about 0.4% Carbopol 980 NF, 5.7% sorbitol, 0.01% cetrimide, 0.01% EDTA, and sodium chloride and sodium hydroxide in adequate amounts to adjust both the viscosity and the pH of the topical carrier to pH 7.0-7.4. Use of the formulation may delay the development of cataracts, reduce retinal degeneration, and maintain normal tear flow in dry eye due to the antioxidant, anti-inflammatory, and chelating activity of the active ingredients.

8 Claims, 7 Drawing Sheets

ANTIOXIDANT EYE DROPS

BACKGROUND OF THE INVENTION

1. Field of the Invention

The present invention relates to topical compositions for reducing, preventing, or reversing damage to the eyes resulting from oxidative stress (dry eye, cataracts, retinal degeneration, etc.), and particularly to antioxidant eye drops containing four nutraceuticals in a carbomer gel carrier.

2. Description of the Related Art

The prevalence of age-related ocular diseases, such as cataract, macular degeneration (AMD) and keratoconjunctivitis sicca (KCS, commonly known as dry eye), increases as populations age. Cataracts account for the majority of reversible age-related vision loss, while AMD is the leading cause of irreversible blindness. KCS, which affects the majority of people over the age of 65, results in significant ocular discomfort and visual dysfunction. While KCS generally does not result in vision loss, KCS, if left untreated, results in painful superficial keratitis that can lead to corneal ulcers or scars.

Age-related diseases are also a growing problem in the veterinary community. Loss of vision from cataracts is the major cause of blindness in dogs and cats. Progressive retinal atrophy with clinical onsets varying from 6 months to 10+ years can also develop in many of these companion pets. These retinal degenerations also have strong genetic links. The onset of dry eye in dogs increases as dogs approach 7-9 years of age. KCS is increased in older female dogs, as compared to male dogs, and is increased in both neutered males and females. In contrast to dogs, the presence of KCS in cats is more subtle.

There is no established pharmaceutical treatment for age-related cataracts, and vision in patients can only be restored by surgery. It has been estimated that the need for cataract surgery can be reduced by 50% by delaying the onset and progression of cataracts by 10 years. The need for a nonsurgical treatment for delaying cataracts is supported by findings that cataract surgery increases the incidence of late AMD. At present, there is also no medical treatment for preventing the onset or reducing the enlargement of geographic atrophy (dry AMD).

The pathogeneses of cataracts and AMD have not been established. However, both are multifactorial diseases with risk factors that include smoking, which is associated with the generation of reactive oxygen species (ROS) and increased tissue iron levels. Dry eye is also a multifactorial disease involving oxidative stress. Smoking also increases the risk of dry eye and exacerbates existing dry eye conditions. Experimentally, increased oxidative damage accompanied by increased levels of iron has been linked to the development and progression of cataracts and AMD. ROS generated in the presence of iron results in the formation of hydroxyl radicals through the Fenton reaction, and also results in mitochondrial dysfunction. Cataracts also develop in patients with hyperferritinemia, an iron disorder associated with increased iron levels. Dysregulation of iron metabolism and iron-handling proteins is also linked to the pathogenesis of AMD, marked by increased chelatable iron observed in the retinal pigmented epithelial cells (RPE) and Bruchs membrane in retinas from AMD patients. Iron overload is also associated with a maculopathy that clinically resembles AMD, including the development and progression of multiple subretinal yellowish-white lesions and RPE cell atrophy in patients with aceruloplasminemia.

Studies indicate that targeting oxidative pathways associated with these age related diseases is therapeutically beneficial. Most formulations containing natural antioxidant and/or vitamins for the support of antioxidant eye health and the reduction of cataract development are orally administered. For example, the oral clinical administration of a combined formulation of natural antioxidants and omega-3 essential fatty acids significantly improves the subjective symptoms of dry eye, while the oral administration of the AREDS natural antioxidant formulation reduces the risk of progression to advanced AMD by 25%. However, several large clinical studies where the nutraceuticals formulations were orally administered suggest that any observed effect of these antioxidants on cataract development is likely to be small and probably of no clinical or public health significance. ROS can also be reduced by lowering tissue levels of iron, which can generate reactive hydroxyl radicals through the Fenton reaction. Studies using chelating agents to reduce iron levels suggest that ROS may also be beneficially reduced in the lens because patients with β-thalassemia receiving chelation therapy with drugs (such as deferoxamine) have a lower incidence of cataracts. Similarly in rats, cataracts from tobacco smoke exposure were reduced by deferoxamine treatment. Novel multifunctional antioxidants with the ability to independently scavenge free radicals and chelate iron have been shown to also delay both cataract formation and protect the retina against light damage, a model for AMD.

Thus, antioxidant eye drops solving the aforementioned problems is desired.

SUMMARY OF THE INVENTION

The antioxidant eye drops is a topical ophthalmic formulation that contains four nutraceuticals (namely, astaxanthin, resveratrol, pyruvate and epigallocatechin gallate (EGCG)) having antioxidant, anti-inflammatory, and chelating activity in a carbomer gel carrier. The active ingredients can reduce oxidative stress through free radical scavenging and chelating activity.

The topical ophthalmic formulation is composed of a mixture of astaxanthin, resveratrol, pyruvate or ethyl pyruvate, and *Camellia sinesis* (green tea extract containing EGCG) in a viscous vehicle composed of a solution of deionized water containing about 0.4% Carbopol 980 NF, 5.7% sorbitol. 0.01% cetrimide, 0.01% EDTA, and sodium chloride and sodium hydroxide in adequate amounts to adjust both the viscosity and the pH of the topical carrier to pH 7.0-7.4. The carbomer vehicle is similar to commercially available Optixcare, which promotes adhesion to the surface of the eye, and has been well-suited to deliver the aldose reductase inhibitor Kinostat™ to diabetic dogs. The range of each individual nutraceutical component can vary from 0.1% to 5% wt/wt. The suggested dose is 1 drop in each eye twice daily (b.i.d.). The topical ophthalmic formulation delays cataracts induced by oxidative stress and reduces retinal degeneration induced by oxidative stress in a human or other mammal. The retinal efficacy can be supplemented with an additional oral capsule containing astaxanthin, resveratrol, pyruvate, and EGCG. The topical ophthalmic formulation also prevents or reduces the reduction of tear flow observed in dry eye.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The antioxidant eye drops (which are also referred to in the present application as Optixcare Eye Health (Optixcare EH)) is a topical ophthalmic formulation that is composed of a mixture of astaxanthin, resveratrol, pyruvate or ethyl pyruvate, and *Camellia sinesis* (green tea extract containing EGCG) in a viscous vehicle composed of a solution of deionized water containing about 0.4% Carbopol 980 NF, 5.7% sorbitol. 0.01% cetrimide, 0.01% EDTA, and sodium chloride and sodium hydroxide in adequate amounts to adjust both the viscosity and the pH of the topical carrier to pH 7.0-7.4. The composition can optionally include 1% ascorbic acid. The ascorbic acid can serve as an antioxidant preservative for the mixture.

Astaxanthin is a carotenoid with 10-fold higher antioxidant activity than zeaxanthin, lutein, canthaxantin, and β-carotene. It is called "super vitamin E" because it has 100-fold higher antioxidant activity than α-tocopherol (vitamin E). In polar solvent, astaxanthin exists in equilibrium with its keto-enol form, which possesses a hydrogen atom capable of breaking the free radical reaction in a manner similar to that of α-tocopherol. There are 3 configurational isomers, 2-enantiomers and a meso form of astaxanthin, with the 3S, 3'S being the most abundant in nature. In vitro, cis-astaxanthin, especially 9-cis-astaxanthin, has higher antioxidant activity than the all-trans isomer.

It has been reported that cultured human lens epithelial cells can accumulate the nutraceuticals astaxanthin, lutein, zeaxanthin and α-tocopherol in a concentration- and time-dependent manner, and all of the former are more potent than α-tocopherol in protecting human lens epithelial cells against oxidative stress produced by UV-B radiation. A 1% suspension of astaxanthin topically administered t.i.d. to Brown Norway Rats over a 9-week period has been reported to reduce cataract formation induced by exposure to UV-B light (1200 mJ/cm$^2$). Streptozotocin induced diabetic rats treated with a diet containing astaxanthin had lower cataracts, and dietary astaxanthin also reduces cataract formation in Atlantic salmon smolts. Various studies have also shown that just as lutein and zeaxanthin are beneficial for the treatment of AMD, astaxanthin has a protective effect on the retina. Astaxanthin slows the decrease in retinal ganglion cells and the thickness of the inner plexiform layer that results from intravitreal injection of N-methyl-D-aspartate (NMDA). In another clinical study, oral administration for 12 months of AZYR tablets (SIFI, Catania, Italy) containing in addition to 4 mg of astaxanthin, 10 mg lutein and 1 mg zeaxanthin, 180 mg of vitamin C, 30 mg vitamin E, 2.5 mg zinc and 1 mg copper to patients with nonadvanced AMD results in a decrease of central retinal dysfunction as measured by multifocal electroretinograms.

Resveratrol is the antioxidant present in red wine, and has been touted as an anti-aging compound. Its antioxidant activity results from the presence of conjugated hydroxyl groups. As reported in the literature, the bioavailability of resveratrol from oral administration is limited, and resveratrol probably does not reach effective target tissue levels because of rapid metabolism by glucoronide and sulfate conjugation by the intestine/liver. Topical application can bypass this metabolism. The protective effects of resveratrol within the eye are extensive, with anti-oxidant, anti-apoptotic, anti-inflammatory, anti-angiogenic and vasorelaxant properties reported. Resveratrol can reduce in a dose-dependent manner of up to 50 μM the secretion of inflammatory cytokines, TGF-β and hypoxia-induced VEGF in primary cultured human retinal pigment epithelial cells (HRPE) cells. In cultured human RPE19 cells, addition of 50 and 100 mmol/L of resveratrol reduces the in vitro proliferation of human RPE19 cells by 10% and 25%, respectively, and protected RPE cells from hydrogen peroxide-induced cell death. Resveratrol is a SIRT1 activator, and upregulation of SIRT1 has been shown to have an important protective effect against various ocular diseases (such as cataract, retinal degeneration, optic neuritis, and uveitis) in animal models. In mice, long-term resveratrol treatment slows age-related degeneration and functional decline in mice, including cataract formation. Resveratrol also ameliorates oxidative stress associated with AMD and glaucoma. In mice with lipopolysaccharide (LPS) injected to induce endotoxin-induced uveitis (EIU), oral administration of resveratrol prior to LPS injections reduces inflammation through inhibition of oxidative damage and redox-sensitive NF-κB activation. In rats with experimental retinal detachment, resveratrol treatment up-regulates the FoxO family and blocks Caspase 3, 8, and 9 activation. In a rabbit corneal culture model, resveratrol reduces the *S aureus* associated expression of interleukin-8 gene.

The presence of astaxanthin in the composition can cause the composition to turn a deep red color. A lighter color can be achieved by decreasing the amount of astaxanthin used and increasing the amount of resveratrol in the composition. For example, a solution or gel containing 1% pyruvate, 1% EGCG, 2% resveratrol, and 0.01% astaxanthin can have a peach color and a viscosity of 18,000-22,000 cps on a Brookfield DV-II Spindle No. T-F at 5 RPM. This gel has a light peach color and a sweet scent.

Pyruvate is an endogenous antioxidant that, when administered as an ethyl ester prodrug, reduces organ system damage in ischemia/reperfusion injury and hemorrhagic and endotoxic shock. Pyruvate has direct beneficial effects on cytokine expression and proinflammatory gene regulation. In in vitro lens and diabetic rat studies reported in the literature, pyruvate delayed sugar cataract formation by decreasing lens sorbitol levels, lipid peroxidation, and promoting the reduction of pyruvate to lactate. It also delays sugar cataracts in 30% galactose-fed rats. Both topically applied sodium pyruvate and its ethyl ester penetrate the cornea. Pyruvate also has radical scavenging ability and can reduce selenite cataracts in rats after i.p. administration, (−)Epigallocatechin gallate (EGCG), the most abundant component in green tea, has 10-fold greater antioxidant activity than vitamin E. As reported in the literature, it can chelate redox reactive iron and copper. When topically applied, it reaches the lens. EGCG reduces ROS associated with UVB radiation and hydrogen peroxide in cultured human lens epithelial cells. It also protects human RPE cells against UVA-induced damage and retina photoreceptors against oxidative stress by sodium nitroprusside. In cultured corneal epithelial cells, EGCG demonstrates anti-inflammatory and anti-oxidant activity. Topical administration of EGCG effectively inhibits corneal neovascularization in rabbits. This inhibitory effect is probably related to the suppression of VEGF and COX-2 mediated angiogenesis. Topical EGCG treatment in mice is able to reduce the clinical signs and inflammatory changes in KCS by suppressing the inflammatory cytokine expression and infiltration of CD11b+ cells in the cornea.

It has been established that diabetic rats rapidly develop diabetic "sugar cataracts" through osmotic stress that is linked to the intracellular accumulation of sorbitol, whose formation is catalyzed by the enzyme aldose reductase. The accumulated sorbitol initiates osmotic stress that induces endoplasmic reticulum (ER) stress that subsequently initiates an unfolded protein response that leads to the generation of ROS. Prevention of sorbitol formation through adequate inhibition of aldose reductase with aldose reductase inhibitors prevents the formation of diabetic cataracts. In contrast, reduction of ROS resulting from ER stress only delays the formation of cataracts.

Several experiments were performed to determine the effectiveness of the composition described above.

EXAMPLE 1

Preparation of a 1 kg Formulation Containing 4% (wt/wt) Active Ingredients

Deionized water (750 g) was added into an appropriate sized stainless steel or glass vessel at room temperature, followed by 0.1 g of cetrimide to give a final concentration of 0.01%, and the mixture was stirred until dissolved. This was followed by the addition of 0.1 g of EDTA with stirring until dissolved to give a final concentration of 0.01%. Next, 57 g of 70% USP Sorbitol was added to give a final concentration of 5.7%, and the mixture was stirred until dissolved. This was followed by the addition of 40 g of resveratrol to give a final concentration of 4.0%. After the solution was well-mixed, 8 g of carbapol 980 was added to give a final concentration of 0.80%, and the mixture was stirred until completely hydrated. This was then followed by the addition of 40 g of ethyl pyruvate and 40 g of Camelia Sinesis extract (EGCG) to give a final concentration of 4% each. This solution was mixed for 5-10 minutes, and 40 g of astaxanthin was added to give a 4% final concentration. After the astaxanthin was dispersed by mixing, the pH was adjusted to 7.0-7.4 with 5N sodium hydroxide solution. Appropriate deionized water was then added to adjust the final water added to 774.8 g (deionized water and hydroxide solution). This concentration was used for the experimental studies.

EXAMPLE 2

Diabetes-Induced Cataracts

For this study, diabetes was induced in young (100 g) Sprague Dawley rats by tail vein injection of 75 mg/kg of streptozotocin, as described by Randazzo et al. (PLoS One, 2011, 6(4), p. e18980). All rats with blood glucose levels >300 mg/dL were then equally divided into 4 groups of 6 each. The first group served as untreated controls, while the second group received 1 drop of the topical aldose reductase inhibitor Kinostat™ to each eye b.i.d. The third group topically received 1 drop of the present antioxidant eye drops composition, prepared as described above and referred to as Optixcare EH, to each eye b.i.d. The fourth group once daily orally received 1 mL of tween 80 Ocu-GLO™ solution, which was prepared by dissolving the contents in capsules of Ocu-GLO™ (Animal Health Quest, Bellingham, Wash.) in an appropriate amount of Tween 80 so that administration of 1 mL of the Tween mixture was delivered per the manufacturer's suggested dosage of nutraceutical formulation per weight of animal. Lens changes were monitored weekly by handheld slit lamp following dilation of each eye with 1% tropicamide ophthalmic solution. Lens changes were evaluated by portable slit lamp using a scale of 0-3, with 0 corresponding to no lens changes; 0.5 corresponding to suture accentuation; 1 to vacuole formation; 2 to cortical opacity; and 3 to mature cataract. The study was terminated 8 weeks after induction of diabetes and the lenses were carefully removed from each enucleated eye using a posterior approach and photo-documented. Blood glucose levels at the onset of the study were determined using a commercial glucometer (Freestyle by TheraSense, Alameda, Calif.). HbA1C levels, which measure the overall hyperglycemia in each rat over the length of the study, were determined at study completion using the Bayer Metrika A1cNOW Plus System test kit (San Diego, Calif.). The results obtained (HbA1C, mean±SEM untreated Control 10.7±0.7; Kinostat™ 11.48±0.2; Optixcare EH 10.6±0.7; Ocu-GLO™ 10.4±0.76) confirmed that rats in all groups were equally diabetic.

Figure 1:
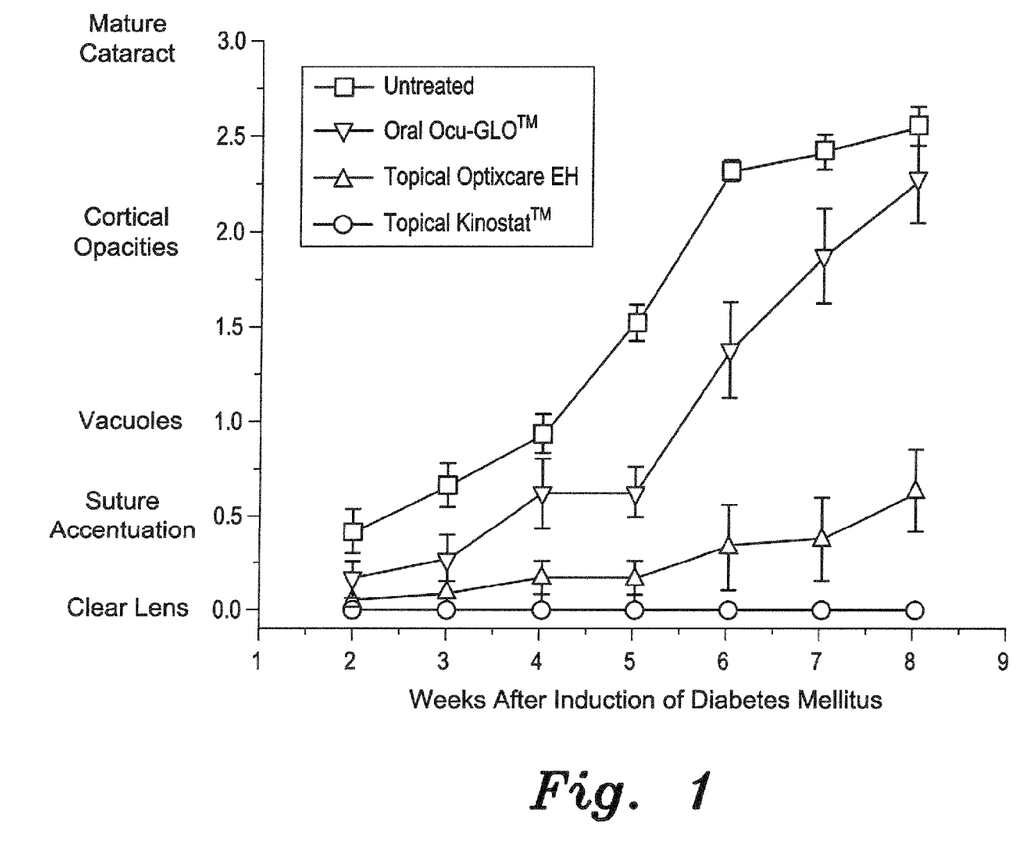
FIG. 1 is a graph showing a comparison of the development of sugar cataracts in rats as a function of the number of weeks after induction of diabetes mellitus in the rats, including a control sample (untreated), a sample treated with antioxidant eye drops according to the present invention (Optixcare EH), and two other commercially available (or soon to be available) eye care formulations.
Figure 2:
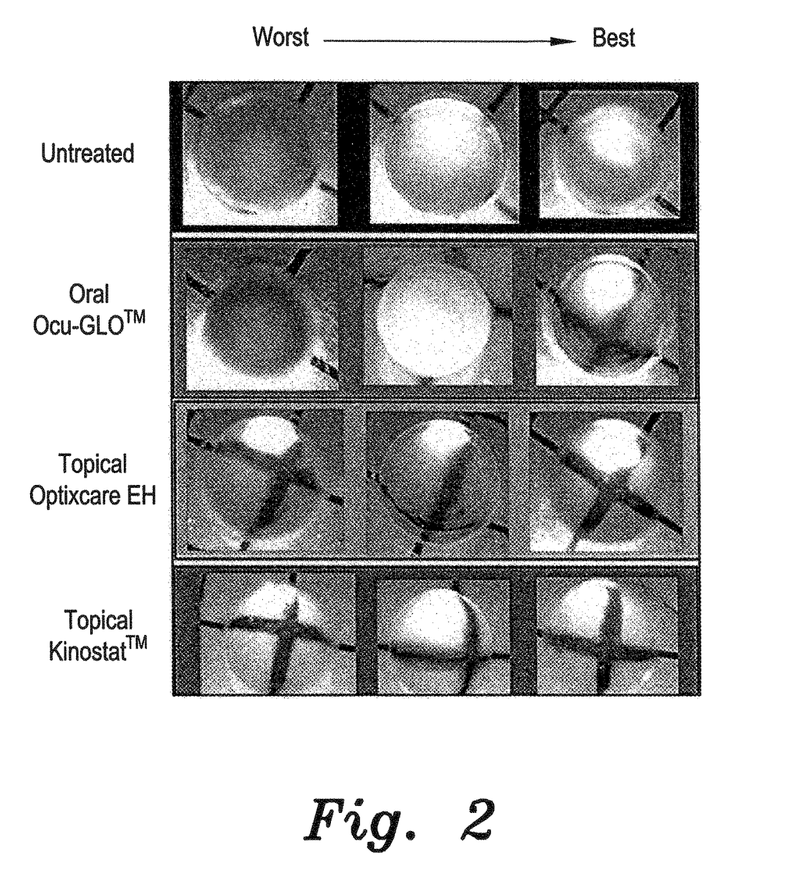
FIG. 2 is a comparative matrix of photomicrographs of the lenses of diabetic rats corresponding to the graph of FIG. 1, showing the relative development of cataracts in the four sample groups of rats.

As summarized in FIG. 1, all young diabetic rats rapidly developed cataracts over an eight-week period, and this formation was prevented by the topical administration of the aldose reductase inhibitor (ARI) Kinostat™. The onset and progression of cataracts in these diabetic rats was delayed by the administration of nutraceuticals with the topical administration of Optixcare EH, demonstrating a greater delay than the oral administration of the Ocu-GLO™. These slit lamp observations were confirmed at the end of the study by microscopic examination of the dissected lenses, as shown in FIG. 2. While no lens opacities were evident in lenses from the ARI treated rats, both the untreated and orally treated Ocu-GLO™ rats developed lens changes ranging from cortical to mature cataracts (FIG. 2). In contrast, primarily suture accentuation, which is the initial stage of sugar cataract development, was present in the Optixcare EH treated diabetic rats.

EXAMPLE 3

UV-Induced Cataracts

Exposure to UV irradiation is another major risk factor of cataractogenesis. UV-irradiation induces ROS, which results in a rapid loss of reduced lens gluthione (GSH), the major antioxidant in the lens, followed several weeks later by subsequent lens opacification. For this study, young female Sprague Dawley rats were divided into five equal groups. One group served as the non-irradiated control group, while the second group served as the untreated irradiated control group. The third group received topical Optixcare carbomer vehicle containing 3% JHX-4 (4-(5-hydroxypyrimidin-2-yl)-N,N-dimethyl-3,5-dioxopiperazine-1-sulfonamide (99% pure by HPLC), the fourth received the present antioxidant eye drops composition, prepared as described above and referred to as topical Optixcare EH, and the fifth group received 1 mL of the oral Ocu-GLO™ by gavage, as described above. Treatments began 3 days prior to irradiation and continued until termination of the experiment. Prior to irradiation, each rat was anesthetized by intraperitoneal (i.p.) injection of a mixture of 60 mg/kg of ketamine and 10 mg/kg of xylazine, and the right eye was dilated with 1% tropicamide ophthalmic solution. The contralateral eye was covered with an eye patch that was held in place with black tape. Each rat was placed on its side with only one eye exposed for 15 minutes to 1600 μw/cm$^2$ of UV light (280-360 nm, $UV_{max}$ 306 nm), while the covered contralateral eye was down and away from UV exposure. Two days after irradiation, each rat was euthanized with carbon dioxide asphyxiation. Both eyes were enucleated and the lenses were carefully removed by a posterior approach. Each lens was homogenized with ice-cold Lysis buffer (pH 7.5), and the insoluble proteins were removed by centrifugation at 4° C. Protein levels in an aliquot of the supernatant were measured according to Bradford Assay. Another aliquot was deproteinized with equal volume of 20% TCA and the GSH levels in the deproteinized supernatants were measured at 412 nm according to the DTNB method.

Figure 3:
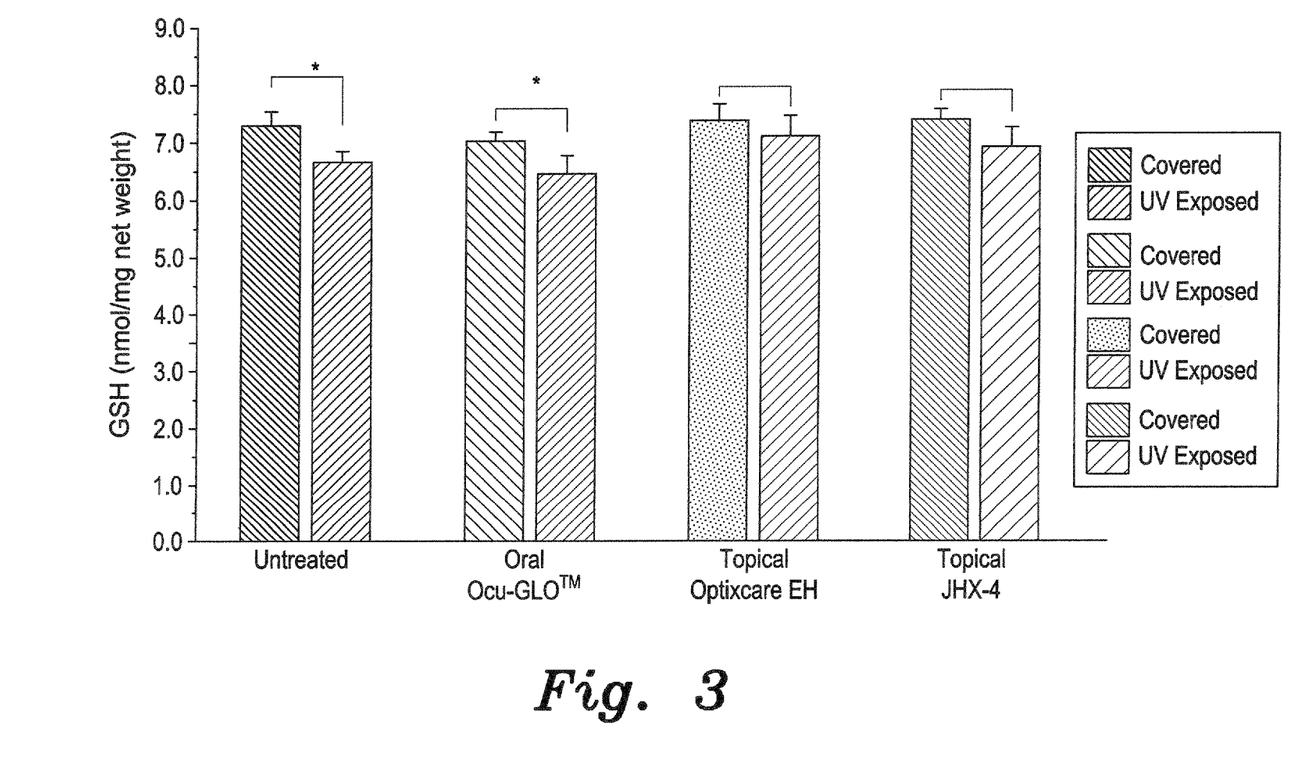
FIG. 3 is a chart showing a comparison of GSH levels in four groups of young female rats where one eye was exposed to UV irradiation while the contralateral eye was covered and served as the non-irradiated control, including a control group (untreated), a group treated with antioxidant eye drops according to the present invention (Optixcare EH), and two groups treated with other eye care formulations.
Figure 4:
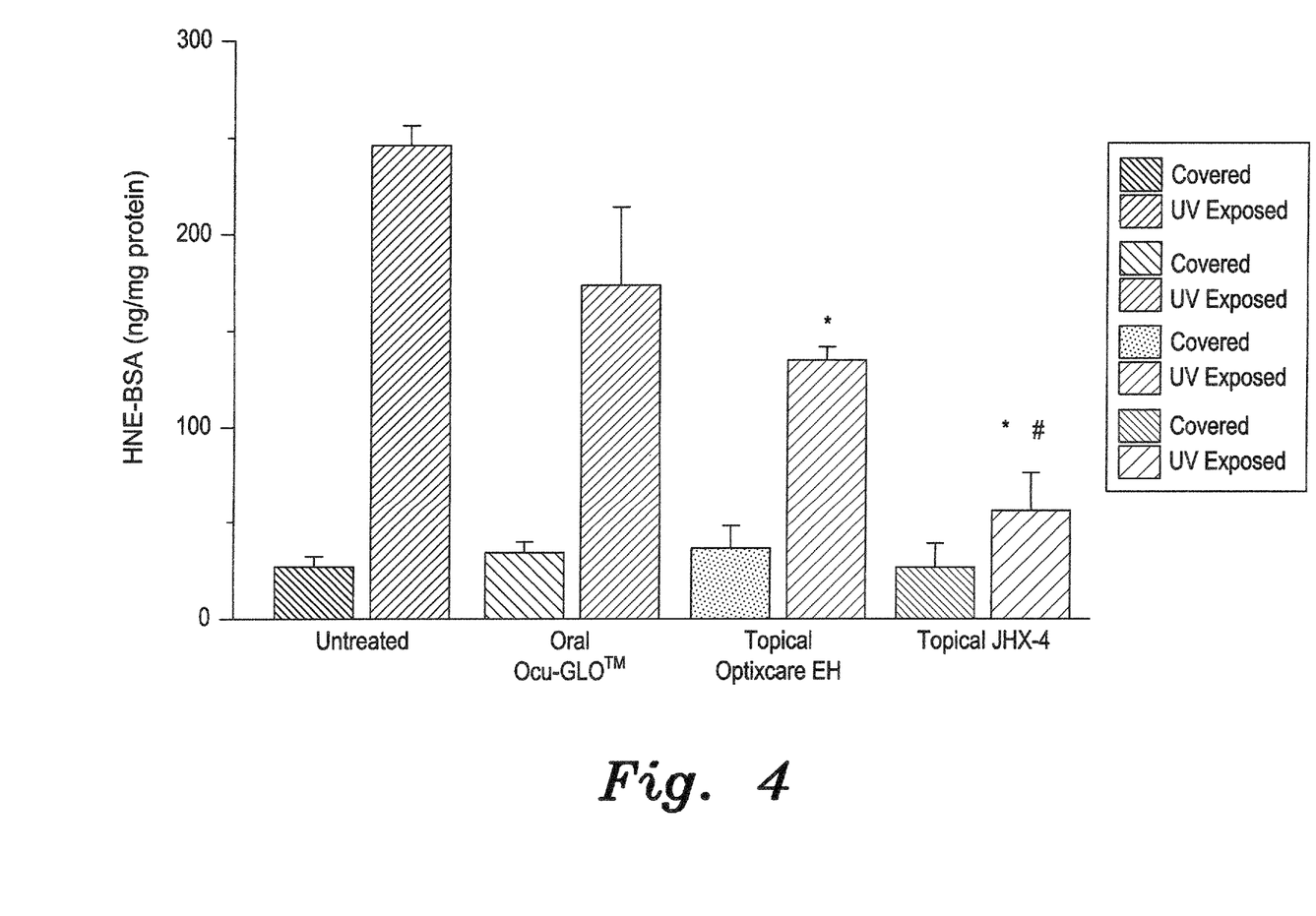
FIG. 4 is a chart showing lenticular levels of 4-hydroxynonenol (4-HNE) in the four sample groups of rats corresponding to FIG. 3.

Evaluation of the lenses in each eye showed that GSH levels were significantly lower ($p<0.05$) in the eyes exposed to UV irradiation compared to GSH levels in their unexposed contralateral lenses, as shown in FIG. 3. Similar irradiation of rats pretreated for 3 days with topical 3% JHX-4 b.i.d., Optixcare EH, b.i.d., or oral Ocu-GLO™ administered daily by gavage, resulted in GSH levels being significantly reduced only in the Ocu-GLO™ treated rats. GSH levels in irradiated lenses from rats topically treated with either Optixcare EH or 3% JHX-4 were not significantly lower (FIG. 3). To confirm that the reduced GSH levels after UV exposure were linked to increased levels of ROS, the lenticular levels of the oxidized membrane lipid 4-hydroxynonenol (4-HNE) were determined using a competitive ELISA in the remaining homogenate supernatants by using the OxiSelect HINE Adduct Competitive ELISA Assay Kit (Cell Biolabs, Inc., San Diego, Calif.) according to the manufacturer's instructions. As summarized in FIG. 4, UV exposure resulted in an increase in 4-FINE levels, which were reduced by antioxidant treatments in the order: topical JHX-4>topical Optixcare EH>oral Ocu-GLO™. Compared to 4-HNE levels in lenses from untreated rats exposed to UV irradiation, 4-HNE levels were significantly lower in UV exposed lenses from rats treated with JHX-4 ($p<0.01$) and Optixcare EH ($p<0.05$). 4-HNE levels in irradiated lenses from the Ocu-GLO™ treated rats were not significantly different than levels in lenses from untreated rats exposed to UV radiation. 4-HNE lens levels from the UV exposed and unexposed contralateral eyes were statistically similar only in the JHX-4 treated rats.

EXAMPLE 4

Light-Induced Retinal Degeneration

In the neural retina of dark adapted rats, exposure to light also results in the generation of ROS, iron dysregulation, and the release of iron from ferritin. In this animal model of age-related macular degeneration (AMD), Wistar rats were either orally treated with diet containing 0.05% of the multifunctional antioxidant JHX-4 or topically treated b.i.d. with Optixcare EH, with treatment beginning at the onset of two weeks of dark adaption.

As previously described in detail by Randazzo et al. (PLoS One, 2011, 6(7), p. e21926), groups containing twelve 4-5-week-old male Wistar rats receiving either normal rat chow (untreated), normal rat chow and topically treated with Optixcare EH b.i.d., or oral diet containing 0.05% of the multifunctional antioxidant JHX-4 were dark adapted for two weeks. Rats from each group were then individually placed into acrylic, flat bottom rodent restraints (Plas-labs, Inc., Lansing Mich.) in a light box apparatus and exposed for three hours to 1000 1× of cool white fluorescent lights (Lights of America, Los Angeles, Calif.). An additional group of non-treated rats were also placed into the light box apparatus for three hours, but not exposed to light (non-light-damaged rats, NLD). Immediately following light exposure, 8 light-damaged (LD) rats from each group and 8 NLD rats were immediately euthanized and the neural retinas were carefully dissected from the enucleated eye and frozen on dry ice for subsequent analysis. Subsequently, the thawed retinas were homogenized in lysis buffer for ELISA determinations using 4-HNE-His Adduct and Nitrotyrosine ELISA Kits. Additional thawed retinas were homogenized in RIPA buffer containing Halt Protease and Phosphatase Inhibitor Cocktail for western blot analysis of thioredoxin (TRx) and thioredoxin reductase (TRxR) expression levels. Protein samples were separated by SDS-PAGE and transferred onto nitrocellulose membranes. After blocking the membrane with 5% dry milk in 0.1% TBS-T, the membranes were then incubated overnight at 4° C. with the primary antibodies anti-TRx (1:1000 dilution) or anti-TRxR (1:2000 dilution). Subsequently, after washing with TBS-T, the membranes were incubated with a HRP-conjugated secondary antibody for 1 hour. The protein bands were visualized by chemiluminescence and exposure to x-ray film. Finally, the membranes were re-probed with antibody against GAPDH as an internal control. All visualized protein levels were quantified using the NIH ImageJ program available online at rsbweb.nih.gov/ij/.

Figure 5A:
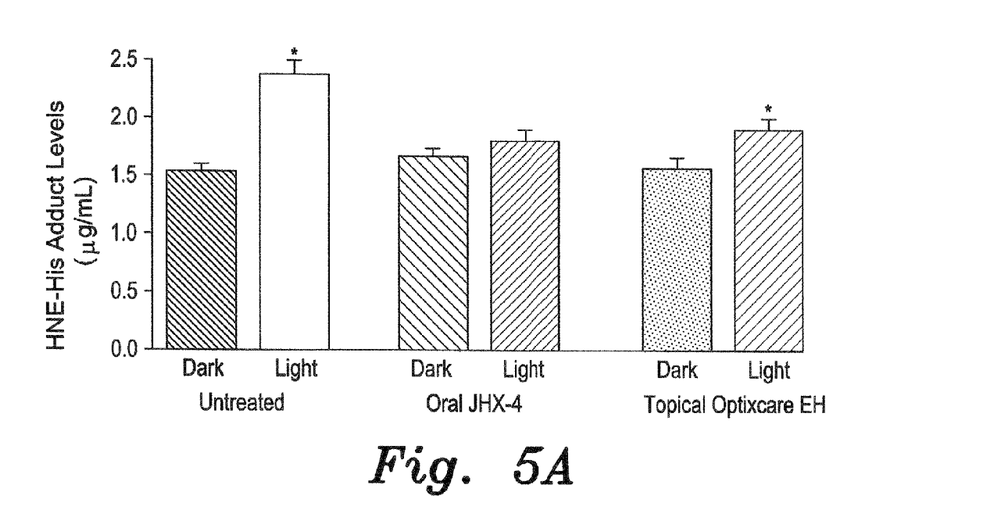
FIG. 5A shows 4-hydroxynonenol (HNE)-histidine adduct levels in the neural retina of three groups of rats exposed to light after a 2-week adaptation to the dark, including a control group (untreated) and a group treated with antioxidant eye drops according to the present invention (Optixcare EH).
Figure 5B:
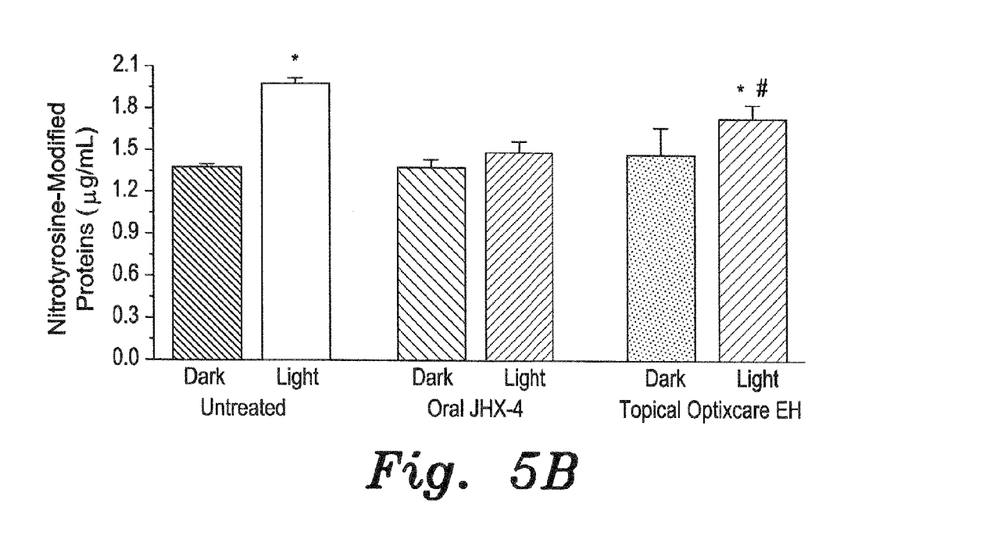
FIG. 5B shows nitrotyrosine adduct levels in the neural retina of the three groups of rats corresponding to FIG. 5A.
Figure 6A:
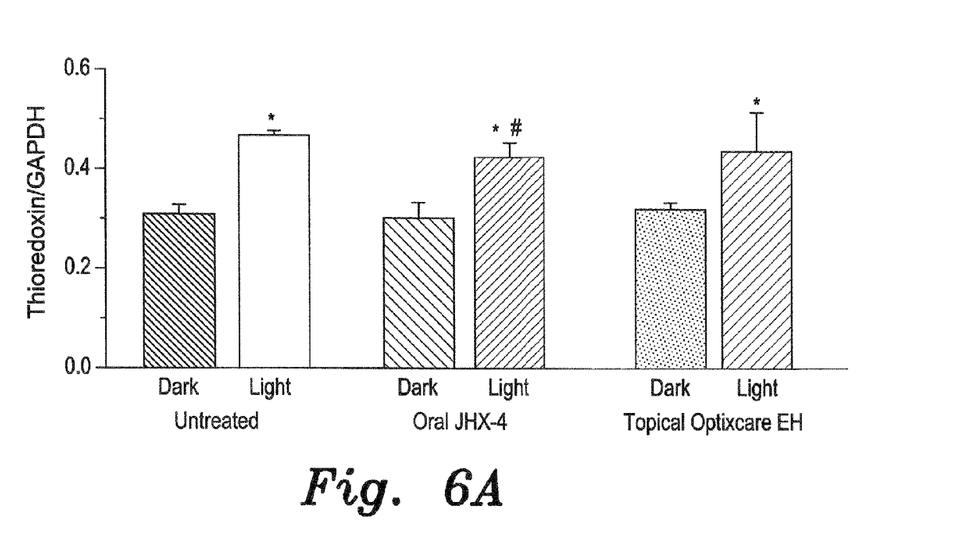
FIG. 6A is a chart showing expression of thioredoxin (TRx) in the neural retina of the three groups of rats corresponding to FIG. 5A.
Figure 6B:
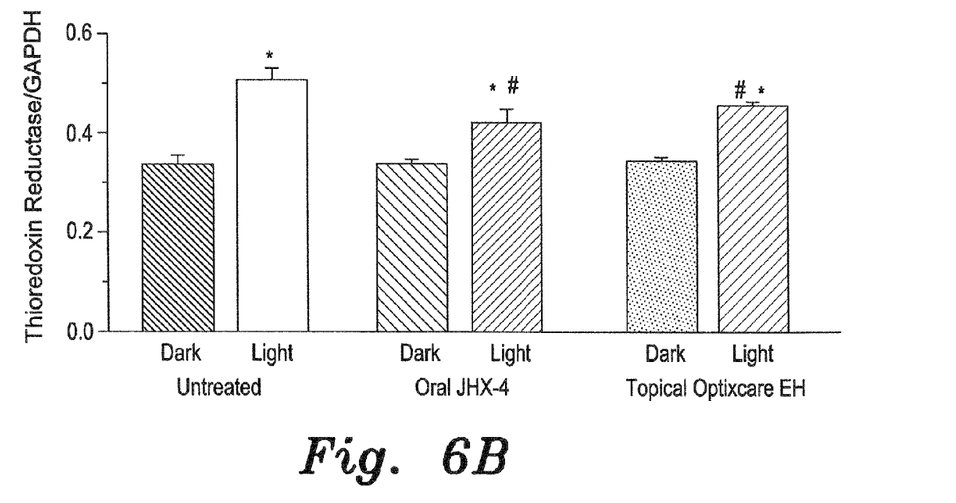
FIG. 6B is a chart showing expression of thioredoxin reductase (TRxR) in the neural retina of the three groups of rats corresponding to FIG. 6A.

In general, topical ocular administration of drugs does not result in adequate retinal levels of drug being obtained. Therefore, topical administration of Optixcare EH to light-exposed dark-adapted rats was not anticipated to result in any significant protection of retinal oxidative stress compared to the oral administration of the multifunctional antioxidant JHX-4. Surprisingly, beneficial retinal antioxidant effects were observed with topically administered Optixcare EH. As reported by Randazzo et al. (PLoS One, 2011, 6(7), p. e21926), exposure of neural retinas to 1000 1× of light for 3 hours resulted in an increase of oxidative stress markers that include 4-HNE adducts formed with histidine following the non-enzymatic oxidation of polyunsaturated fatty acids (see FIG. 5A) and nitrotyrosine-modified proteins resulting from tyrosine residues being oxidized by peroxynitrite formed by the reaction of nitric oxide with superoxide anions (see FIG. 5B). After light exposure, both of these markers significantly increased, while neither oxidative marker significantly increased in similar light-exposed rats treated with JHX-4 (FIGS. 6A, 6B). Rats treated with Optixcare EH showed partial increases in both oxidative markers. However, these increases were significantly less than those in untreated rats. ROS and free radicals generated by retinal exposure to acute excessive light are also mediated by the thioredoxin (TRx)/thioredoxin reductase (TRxR) defense system. Therefore, the expression levels of both TRx and TRxR in the neural retinas of these rats were also examined. Both TRx and TRxR expression increased in untreated rats exposed to light, as shown in FIGS. 6A, 6B. The expression of TRxR was significantly lowered (p<0.05) in the neural retinas of light exposed rats treated by either JHX-4 or Optixcare EH. However, TRx expression was only reduced by JHX-4.

The reduction of oxidative stress by JHX-4 and Optixcare EH was confirmed by histological measurements of the photoreceptor layers. After light exposure as described above, select rats in each group were returned to the dark environment for 7 additional days. Each rat was then euthanized by carbon dioxide asphyxiation, and the dorsal ventral orientation of each eye was marked with a cautery tool. The eyes were then enucleated, fixed in a 3:1 (v/v) methanol; acetic acid solution overnight, and processed by standard histological methods. Digital images of the H&E stained sections were obtained using a Zeiss AxioPlan microscope (Carl Zeiss MicroImaging, Inc., Thornwood, N.Y.) using Axiovision software. The outer nuclear layer (ONL) thickness was measured at 400 µm intervals, starting at the optic nerve head and extending toward the superior and inferior ora serrata using Image-Pro Plus software (Media Cybernetics, Silver Spring, Md.). Results showed that the intense light exposure resulted in photoreceptors thinning in the outer nuclear layer (ONL), with damage in the superior hemisphere more pronounced than the inferior hemisphere. In rats treated with JHX-4, the photoreceptor layer was only slightly decreased, both in the inferior hemisphere and superior hemisphere. In contrast, the photoreceptor layer was only partially protected in the Optixcare EH treated rats. These results suggest that despite topical delivery, Optixcare EH can partially reduce oxidative stress in the retinas of light damaged rats.

EXAMPLE 5

Scopolamine-Induced Dry Eye

Figure 7:
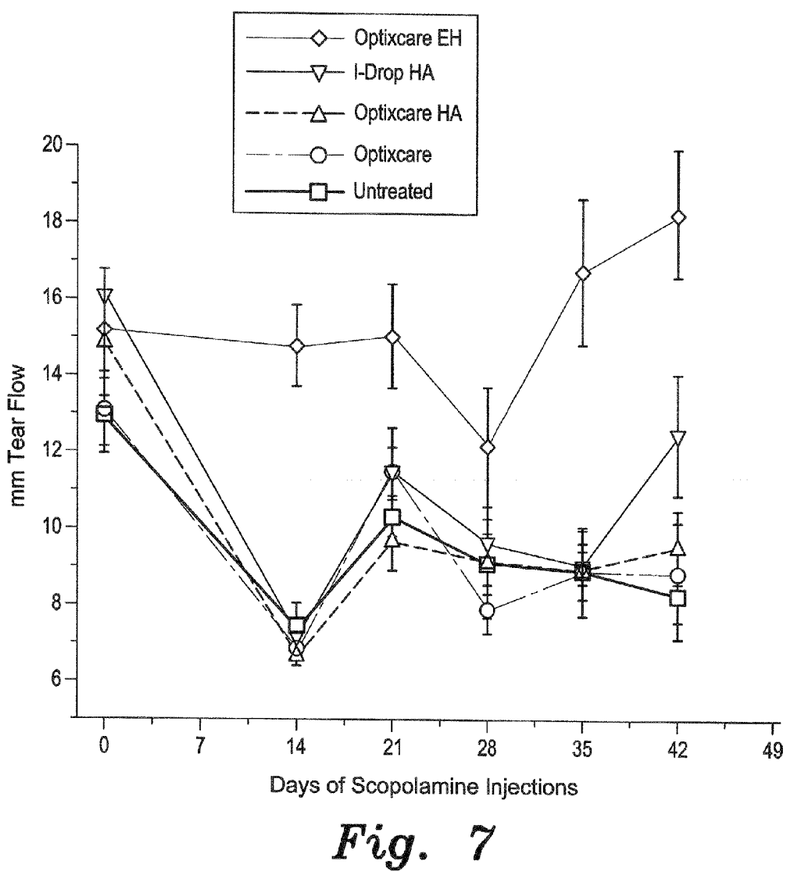
FIG. 7 is a graph showing tear flow induced by twice daily subcutaneous injections of scopolamine in five groups of adult Lewis rats, including a control group (untreated) and a group treated with antioxidant eye drops according to the present invention (Optixcare EH).

Optixcare is a commercially available carbomer-based eye lubricant that is used in the veterinary market to protect eyes from dehydration during anesthesia and as adjunctive support for dry eyes. Optixcare belongs to a class of ocular comfort agents that is composed of poly(acrylic acid) polymers that are designed to relieve ocular discomfort by augmenting the characteristics of the tear film so that the tear volume is stabilized and retained, while the ocular surface remains lubricated. Other such agents include hyaluronic acid, which retains water. Since Optixcare, Optixcare H (Optixcare containing hyaluronic acid) and the hyaluronic formulation Idrop Vet Plus Opthalmic Solution (topical hyaluronic acid from imed Pharma, Dollard-dcs-Ormeaux, Canada) are used in the veterinary market for alleviating the clinical symptoms of dry eye, the potential effect of Optixcare EH on actually treating dry eye was investigated because the ingredients in Optixcare EH possess not only antioxidant, but also anti-inflammatory activity. Dry eye was induced in thirty 180-200 g female Lewis rats, which were divided into 5 groups. One served as an untreated control, while each of the other groups received 1 drop of either Optixcare, Optixcare H, Idrop Vet Plus Opthalmic Solution, or the present antioxidant eye drops composition (Optixcare EH) in each eye twice daily. Dry eye was induced in all rats by twice-daily subcutaneous injection of a 0.1 mL aqueous solution containing 24 mg of scopolamine (48 mg total dosage per day). Tear flow was measured weekly prior to dosing using Zone-Quick™ Phenol Red Threads (FCI Opthalmics, Pembroke, Mass.) by anesthetizing each rat with isofluorane. The lower eyelid was pulled down, and using forceps, the folded 3 mm end of each thread was placed into the palpebral conjunctiva at a point approximately ⅓ of the distance from the lateral canthus. The string was left in the open eye for 15 seconds and then removed by gently pulling the lower eyelid down and removing the thread with an upward motion. The length of red-stained thread was then immediately measured. As summarized in FIG. 7, tear flow in each rat, determined as the average of both eyes, decreased over time in the untreated rats, and topical administration of any of the comfort agents Optixcare, Optixcare H, or i-Drop hyaluronic acid did not alter this decrease in tear flow. In contrast, tear flow was preserved in similar scopolamine injected rats receiving the present Optixcare EH composition. This indicated that the addition of nutraceuticals antioxidants alter the ability of Optixcare to serve as an adjunctive treatment for dry eye.

The composition can be disposed in and/or dispensed from a low density polyethylene (LDPE) tube, e.g. a 15 g., white, low-density polyethylene (LDPE) tube. The tube can include five layers, including an ethylene vinyl alcohol copolymer barrier sandwiched with adhesive between each two layers of the polyethylene. The tube can include, for example, a dispenser tip with a 0.047" orifice and a smooth, threaded closure that is ⅞" in diameter.

It is to be understood that the present invention is not limited to the embodiments described above, but encompasses any and all embodiments within the scope of the following claims.

I claim:

1. An eye drop dispenser and an antioxidant eye drop composition consisting essentially of:
    0.01% centrimide;
    5.7% sorbitol;
    4% green tea extract containing (−)Epigallocatechin gallate; and
    the balance being a carbomer gel carrier.

2. An eye drop dispenser and an antioxidant eye drop Composition consisting essentially of:
    about 4% pyruvate or ethyl pyruvate;
    about 4% resveratrol;
    about 4% astaxanthin;
    about 4% green tea extract containing (−)Epigallocatechin gallate; and
    the balance being a carbomer gel carrier, wherein the carbomer gel carrier consists essentially of:
        about 0.4% Carbopol 980 NF;
        about 5.7% sorbitol;
        about 0.01% cetrimide;
        about 0.01% EDTA; and
        the balance being deionized water.

3. A method of reducing cataracts induced by oxidative stress in a human in need thereof, consisting essentially of a step of topically administering from the eye drop dispenser of claim 2 the composition of claim 2 to the human in need thereof.

4. The method of reducing cataracts according to claim 3, wherein said composition is a dose of 1 drop of the antioxidant eye drop composition which is administered in each of the eye of the human in need thereof twice daily.

5. A method of reducing retinal degeneration induced by oxidative stress in a human in need thereof, consisting essentially of a step of topically administering from the eye drop dispenser of claim 2 the composition of claim 2 to the human in need thereof.

6. The method of reducing retinal degeneration according to claim 5, wherein said composition is a dose of 1 drop of the antioxidant eye drop composition which is administered in each eye of the human in need thereof twice daily.

7. A method of reducing the reduction of tear flow observed in dry eye induced by oxidative stress in a human in need thereof, consisting essentially of a step of topically administering from the eye drop dispenser of claim 2 the composition of claim 2 to the human in need thereof.

8. The method of reducing the reduction of tear flow observed in dry eye according to claim 7, wherein said composition is a dose of 1 drop of the antioxidant eye drop composition which is administered in each eye of the human in need thereof twice daily.

\* \* \* \* \*